United States Patent [19]
Lizcano

[11] Patent Number: 6,053,931
[45] Date of Patent: Apr. 25, 2000

[54] EAR PIERCING TEMPLATE APPARATUS

[76] Inventor: Elizabeth C. Lizcano, 6940 Sherman, Houston, Tex. 77011

[21] Appl. No.: 09/166,455

[22] Filed: Oct. 5, 1998

[51] Int. Cl.[7] .................................................. A61B 17/00
[52] U.S. Cl. ............................................................ 606/188
[58] Field of Search ............................. 606/188; 604/116

[56] References Cited

U.S. PATENT DOCUMENTS

| | | |
|---|---|---|
| 2,245,350 | 6/1941 | Marshall . |
| 3,542,022 | 11/1970 | Bartnik .................................... 604/116 |
| 4,020,848 | 5/1977 | DiCicco . |
| 4,068,668 | 1/1978 | Moore et al. . |
| 4,267,838 | 5/1981 | McCall . |
| 4,362,157 | 12/1982 | Keeth . |
| 5,247,946 | 9/1993 | Holder . |

*Primary Examiner*—Michael Buiz
*Assistant Examiner*—William W. Lewis

[57] ABSTRACT

An ear piercing template apparatus provides a body defining at least one aperture therethrough. The body is adapted to be positioned against an ear to be pierced and allow the piercing stud to pass through the aligned aperture while the ear piercing device abuts the body. The body, which is substantially rigid, maintains the relative angle between the ear and the ear piercing device and ensures that the resulting hole is aligned properly. The ear piercing template apparatus is then used to align the pierced hole on the opposite ear. To facilitate this alignment, the body is transparent and includes indicia thereon, such as aperture labels, angle markings, and measurement markings. A support member holds the body on the ear making use of the ear piercing template apparatus easier and increasing repeatability. A system provides a plurality of the ear piercing template apparatuses, each having a different size.

9 Claims, 5 Drawing Sheets

FIG. 13 ically, ear piercing is completed by placing a stud
EAR PIERCING TEMPLATE APPARATUS

BACKGROUND OF THE INVENTION

1. Field of Invention

The present invention relates to the field of ear piercing devices. More specifically, the invention relates to a device system, and method for use in ear piercing that provides a template that facilitates straight pierces and proper alignment on the ears.

2. Related Art

Ear piercing has long been a popular means of providing ornamentation for many men and most women in the U.S. Often, a person will have multiple pierces through each ear so that they may wear multiple earrings.

Figure 1:
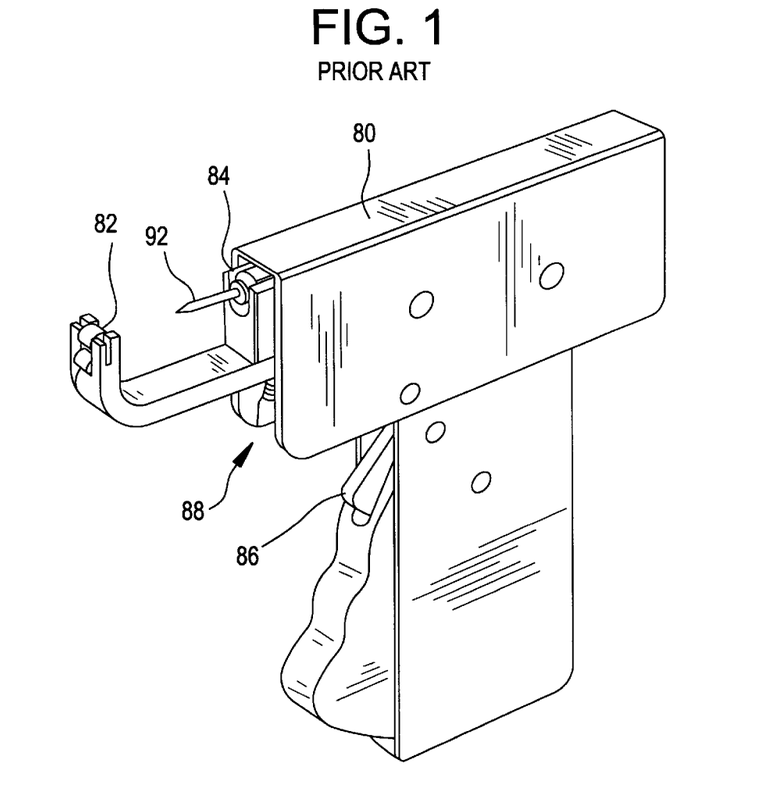
FIG. 1 is a perspective view of a prior art ear piercing device.

Typically, ear piercing is completed by placing a stud (having a head and a wire portion; see FIG. 2) of a stud assembly in an outer clamp of an ear piercing device (FIG. 1). A clasp of the stud assembly is held in an inner clamp of the ear piercing device with its central receiving hole aligned with the wire of the stud. The ear piercing device is then positioned with the inner clamp behind the ear, the outer clamp outside the ear, and the wire of the stud aimed at the desired location of the pierce. Once properly positioned, a trigger of the ear piercing device releases an actuating member which forces the wire of the stud through the ear and into the clasp. The stud and clasp are then released from the ear piercing device. In this way, the stud pierces the ear.

One problem associated with the piercing of ears involves the proper alignment of the resulting pierced hole with the ear. If the stud is not properly aligned with the ear during insertion, the resulting pierced hole through the ear is misaligned. A misalignment may result from the operator not holding the ear piercing device in proper alignment with the ear, from the recipient, anticipating pain, moving during the procedure, or from other, similar occurrences. If the pierced hole is misaligned, an earring placed in the hole will not be properly aligned. The misalignment is often apparent with larger earrings, such as hoop earrings, because one will align in one direction relative to the wearer's face whereas the other earring will align in a different direction relative to the wearer's face. Such a result is not desired.

Another problem associated with the piercing of ears involves the proper alignment of the resulting pierced holes on the ears with one another. To align the pierced holes with one another, the operator typically uses a ruler or other standard measuring device to measure the distance from a certain position on the ear, such as the bottom of the ear lobe, and marks the position with a surgical pen. Such positioning involves some guesswork and estimating often resulting in improper positioning of the pierced holes relative to one another. The resulting holes are often misaligned with one another vertically and horizontally and are often positioned on their respective ear in a different place than the other. The result is an undesirable misalignment of the pierced holes.

Thus, there is a need for a device, system, and method for facilitating alignment of the pierced holes with the ear and with one another.

SUMMARY OF THE INVENTION

To achieve such improvements, the present invention provides an ear piercing template apparatus that facilitates alignment and positioning of an ear piercing stud during ear piercing. In general, the ear piercing template apparatus provides a body having opposing sides and a periphery and at least one aperture extending through the body. The body and the at least one aperture are sized and adapted to provide passage of the ear piercing stud therethrough. In use, the ear piercing template apparatus is positioned against the ear and one of the apertures is aligned with the desired piercing location. The ear piercing device is then used to pierce the ear through the aligned aperture. The substantially rigid body of the ear piercing template apparatus abuts the ear piercing device and the ear and reduces relative angular movement therebetween increasing the accuracy of the alignment of the pierced hole through the ear. Also, the ear piercing template apparatus is then positioned against the opposite ear and used to align the pierced hole with the ear. The apertures of the ear piercing template apparatus facilitate alignment of the ear pierces on the ears relative to one another.

One aspect of the invention provides an ear piercing template apparatus for use with an ear piercing device of the type that uses a stud to pierce an ear. The apparatus comprises a body having opposing surfaces and a periphery and at least one aperture extending through the body. The body and the at least one aperture are sized and adapted to provide passage of the stud therethrough. In one embodiment, the opposing surfaces are substantially flat and the body is relatively thin. Additionally, the opposing surfaces are substantially parallel.

In one alternative embodiment the body has an outer surface and an inner surface and defines a recess about each of the at least one apertures. The recess is formed in the outer surface and has a size and shape similar to that of an outer clamp of an ear piercing device so that the recess is adapted to receive the outer clamp therein.

Preferably, the body is formed of a material capable of being sterilized, is substantially rigid, and is at least partially transparent.

In another alternative embodiment, the body comprises a rigid member, having an inner surface and an outer surface, and a cushion, having an inner surface and an outer surface. The outer surface of the cushion is attached to the inner surface of the rigid member; the inner surface of the cushion defines an inner surface of the body; and the outer surface of the rigid member defines an outer surface of the body. The rigid member is substantially rigid; and the cushion is adapted for abutment with the ear and is preferably formed of a resilient material. In an alternative embodiment, the inner surface of the cushion has a shape that substantially conforms to an ear.

In the preferred embodiment, the body is sized such that the periphery of the body covers the ear and the body has a periphery that is shaped substantially similar to an ear.

In one embodiment the body defines a plurality of apertures. To align the apertures with the typical piercing locations, the plurality of apertures are spaced about the body proximal to the periphery of the body.

In alternative embodiments, the at least one aperture comprises a hole through the body, a slot extending to the periphery of the body, and at least one slot through the body, the slot extending parallel and proximal to the periphery of the body and about a portion of the periphery.

In addition, the apparatus preferably also comprises indicia on at least one surface of the body. In varying embodiments, the indicia comprises aperture labels, angle markings, and/or measurement markings, among many other possibilities.

Yet another alternative embodiment of the invention provides a support member attached to the body that is adapted to maintain the body on the ear. One embodiment of the support member comprises an earpiece; while another comprises a clip. An alternative embodiment also comprises a position adjustment member that is adapted to provide for adjustment of the position of the body relative to the ear.

Another aspect of the invention provides an ear piercing template system for use with an ear piercing device of the type that uses a stud to pierce an ear. The system comprises a plurality of ear piercing apparatuses each formed as previously described and each with a different size than the others.

Yet another aspect of the invention provides a method for piercing an ear using an ear piercing template apparatus and an ear piercing device of the type that uses a stud to pierce an ear. The method comprises positioning the ear piercing template apparatus against the ear with at least one aperture of a body of the ear piercing template apparatus aligned with the desired piercing location on the ear; aligning a stud held within the ear piercing device with the desired piercing location on the ear; and actuating the ear piercing device to pierce the ear at the desired piercing location on the ear.

BRIEF DESCRIPTION OF THE DRAWINGS

The manner in which these objectives and other desirable characteristics can be obtained is explained in the following description and attached drawings in which.

It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

The present invention generally provides an ear piercing template apparatus that facilitates alignment and positioning of an ear piercing stud during ear piercing. In general, the ear piercing template apparatus provides a body having opposing sides and a periphery and at least one aperture extending through the body. The body and the at least one aperture are sized and adapted to provide passage of the ear piercing stud therethrough. In use, the ear piercing template apparatus is positioned against the ear and one of the apertures is aligned with the desired piercing location. The ear piercing device is then used to pierce the ear through the aligned aperture. The substantially rigid body of the ear piercing template apparatus abuts the ear piercing device and the ear and reduces relative angular movement therebetween increasing the accuracy of the alignment of the pierced hole through the ear. Also, the ear piercing template apparatus is then positioned against the opposite ear and used to align the pierced hole with the ear. The apertures of the ear piercing template apparatus facilitate alignment of the ear pierces on the ears relative to one another.

Figure 2:
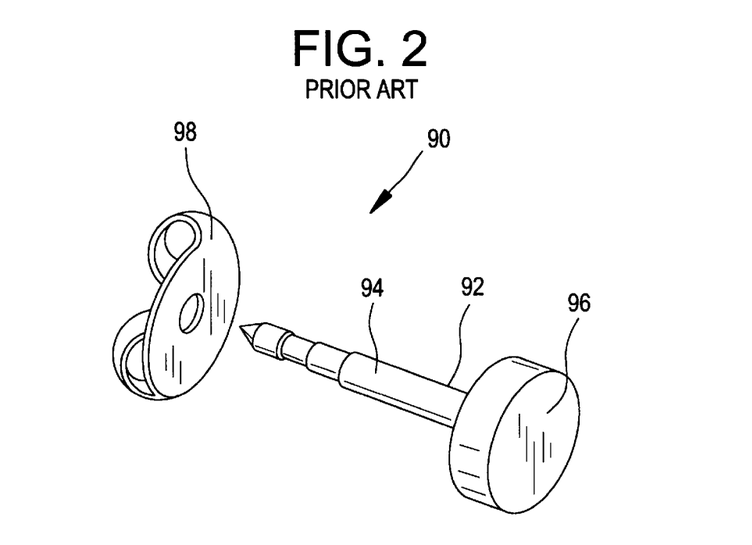
FIG. 2 is a perspective view of a prior art stud assembly.

FIG. 1 shows a typical ear piercing device 80. In general, the ear piercing device 80 comprises an inner clamp 82, an outer clamp 84, a trigger 86, and an actuating member 88. FIG. 2 shows a standard stud assembly 90 used in piercing ears. The stud assembly 90 generally comprises a stud 92, having a wire portion 94 and a head portion 96, and a clasp 98. The clasp 98 is adapted to fit around the wire portion 94 of the stud 92 and maintain the stud 92 on the ear 2.

The outer clamp 84 of the ear piercing device 80 is adapted to hold the stud 92 with the wire 94 pointing away from the main body 20 of the ear piercing device 80. The inner clamp 82 is adapted to hold the clasp 98 in spaced relation (initially) to the stud 92 with the hole of the clasp 98 aligned with and positioned for receipt of the wire 94 of the stud 92. To facilitate piercing, the inner and outer clamps 82, 84 of the ear piercing device 80 are selectively movable relative to one another. However, the clamps are maintained in an initial, spaced position until the stud 92 is properly aligned with the desired location of the pierce. Once properly positioned with the inner clamp 82 behind the ear 2 and the outer clamp 84 on the opposite side of the ear 2, the trigger 86 of the ear piercing device 80 is actuated allowing the actuating member 88 to move the clamps of the ear piercing device 80 toward one another. The movement of the clamps toward one another forces the wire 94 of the stud 92 through the ear 2, piercing the ear 2. The wire 94 enters the clasp 98 joining the stud assembly 90 and holding the stud assembly 90 on the ear 2. The description of the ear piercing device 80 and the stud 92 is informative only and lays a foundation for the description of the invention. Note that the present invention will work with most types of standard, known ear piercing devices 80 regardless of the manner in which they function. Examples of ear piercing devices 80 are shown in U.S. Pat. Nos. 4,020,848 and 4,068,668 which are hereby incorporated by reference herein.

Figure 3:
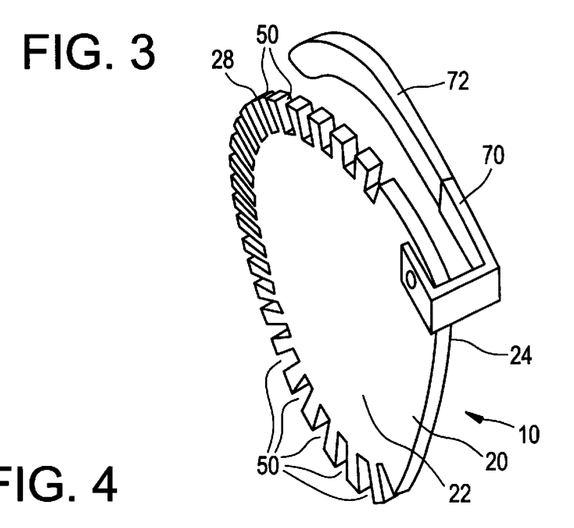
FIG. 3 is a perspective view of one embodiment of the ear piercing template apparatus.

FIG. 3 is a perspective view of one embodiment of the present invention. In general, the ear piercing template apparatus 10 provides a body 20 having at least one aperture 50 therethrough. The body 20 and the aperture 50 are sized and adapted to provide passage of the stud 92 therethrough. The body 20 has an inner surface 22 and an outer surface 24 which oppose one another and a periphery 28. In the embodiment shown in the figure, the inner and outer surfaces 22, 24 are relatively flat and substantially parallel. As is further discussed below, the ear piercing template apparatus 10 is positioned between the ear 2 and the stud 92 prior to piercing of the ear 2. Thus, to facilitate passage of the stud 92 through the body 20 and facilitate use of the ear piercing template apparatus 10 with standard ear piercing devices 80, the body 20, in the embodiment shown in the figure, is relatively thin.

Preferably, the body 20 is formed of a substantially rigid material that is capable of being sterilized although some flexibility is acceptable. Some examples of acceptable materials include stainless steel and certain plastics among other materials. The rigidity of the body 20 helps ensure that the ear piercing template apparatus 10 maintains the relative angular positioning of the ear 2 and the ear piercing device 80. In this way, the ear piercing template apparatus 10 ensures that the pierced hole is made at the proper angle.

The body 20 has an outer shape that resembles that of a typical ear 2. So that the template may be easily used to pierce any position of the ear 2, the ear piercing template apparatus 10 is also approximately the same size as the ear 2. However, not all ears are the same size. Therefore, the ear piercing template apparatus 10 preferably comes in a variety of sizes ranging from those suitable for use on a child's ear to those suitable for an adult having relatively large ears. Such a ear piercing template system comprising a plurality of ear piercing template apparatuses 10 includes at least two such apparatuses and, preferably, at least four ear piercing template apparatuses 10.

The ear piercing template apparatus 10 shown in the figure defines a plurality of apertures 50 spaced about the periphery 28 of the body 20. In this embodiment, the apertures 50 each comprise a slot that is open to the periphery 28 of the body 20. Providing the opening to the periphery 28 allows the ear piercing template apparatus 10 to be pulled from between the stud 92 and the ear 2 after the piercing operation is complete. Thus, the slots may be relatively small and need only be slightly larger than the wire 94 of the stud 92. Therefore, since the slots may be narrower than the diameter of the head 96 of the stud 92, the body 20 can include more slots positioned nearer one another. This allows more possible piercing locations about the ear piercing template apparatus 10 and the ear 2. The slots extend into the body 20 sufficiently far that the ear 2 may be pierced through the slot at a variety of positions relative to the periphery 28 of the body 20. Consequently, the slots positioned for use in piercing the lobe of the ear 2 are typically longer than those for use in piercing the top of the ear 2. Thus, the length of the slots may vary depending upon their position on the ear piercing template apparatus 10 and their length is adapted to allow piercing of the full range of the outer portion, including the full lobe, of the ear 2.

The ear piercing template apparatus 10 preferably includes a support member 70 for supporting the ear piercing template apparatus 10 on the ear 2. In the embodiment shown in FIG. 3, the support member 70 is an earpiece 72 attached to the body 20 of the ear piercing template apparatus 10. The earpiece 72 shown is similar to a typical earpiece used with glasses and is adapted and positioned to be placed behind the ear 2 and to rest upon the ear 2 holding the ear piercing template apparatus 10 in place. Preferably, the earpiece 72 is adjustable so that it may be adjusted according to the needs of the wearer. One manner of making the earpiece 72 adjustable is to use a material that may be deformed without causing permanent damage and that holds its shape and position once deformed. Many standard eyeglass earpieces include such a design and typically comprise a small-diameter wire which may be encased in plastic or rubber.

By providing a support member 70, the positioning of the ear piercing template apparatus 10 relative to the ear 2 becomes repeatable increasing the accuracy of the ear piercing template apparatus 10 when used to align the pierced holes through the ears relative to one another. The earpiece 72 aligns the ear piercing template apparatus 10 relative to the top of the ear regardless of the ear to which it is attached increasing repeatability.

Figure 4:
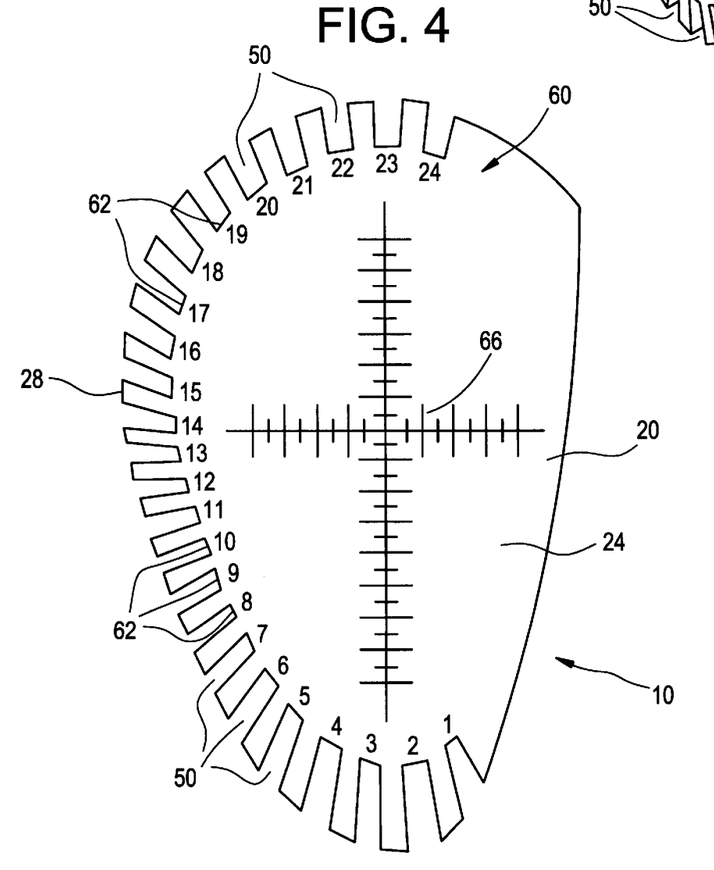
FIG. 4 is an elevational view showing an embodiment of the ear piercing template apparatus.

FIG. 4 is a front elevational view of an embodiment of the ear piercing template apparatus 10. The embodiment shown in FIG. 4 has a plurality of slots similar to those shown in FIG. 3. As shown in the figure, the length of the slots varies depending upon their position about the body 20. Those proximal the ear lobe portion of the ear piercing template apparatus 10 are longer (i.e., extend further into the body 20) than those positioned elsewhere on the body 20.

The surface of the ear piercing template apparatus 10 provides indicia 60 thereon to facilitate alignment of the ear piercing template apparatus 10 and the resulting pierced hole. In the embodiment shown in FIG. 4, the indicia 60 comprises aperture labels 62 in the form of sequential numbers associated with each of the apertures 50. The aperture labels 62 are particularly useful in aligning the pierce locations on the respective ears in that the operator may align the ear piercing device 80 with the same numbered aperture 50 on each ear. In other words, the operator may pierce the ear through aperture number 4, for example, on one ear and then pierce the other ear through aperture number 4. Of course the aperture labels 62 may take any form including, inter alia, numbers, letters, words, designs, pictures, and the like.

The embodiment shown in FIG. 4 also provides indicia 60 on the surface of the ear piercing template apparatus 10 in the form of measurement markings 66. The measurement markings 66 include a vertical, straight line and a horizontal straight line which intersect one another proximal the center of the body 20. Measurement bars spaced along each of the lines at predetermined intervals provide a measurement tool for the operator. Using the measurement markings 66, the operator may align the ear piercing template apparatus 10 with certain aspects of the ear and may use the lines to align the ear piercing template apparatus 10 vertically and horizontally. Thus, using the measurement markings 66, the ear piercing template apparatus 10 may be aligned with each of the ears more accurately and may be positioned in the same relative position on each ear. Thereby, the measurement marking increase accuracy and repeatability.

Note that the shape of the ear piercing template apparatus 10 is generally the shape of an ear.

Figure 5:
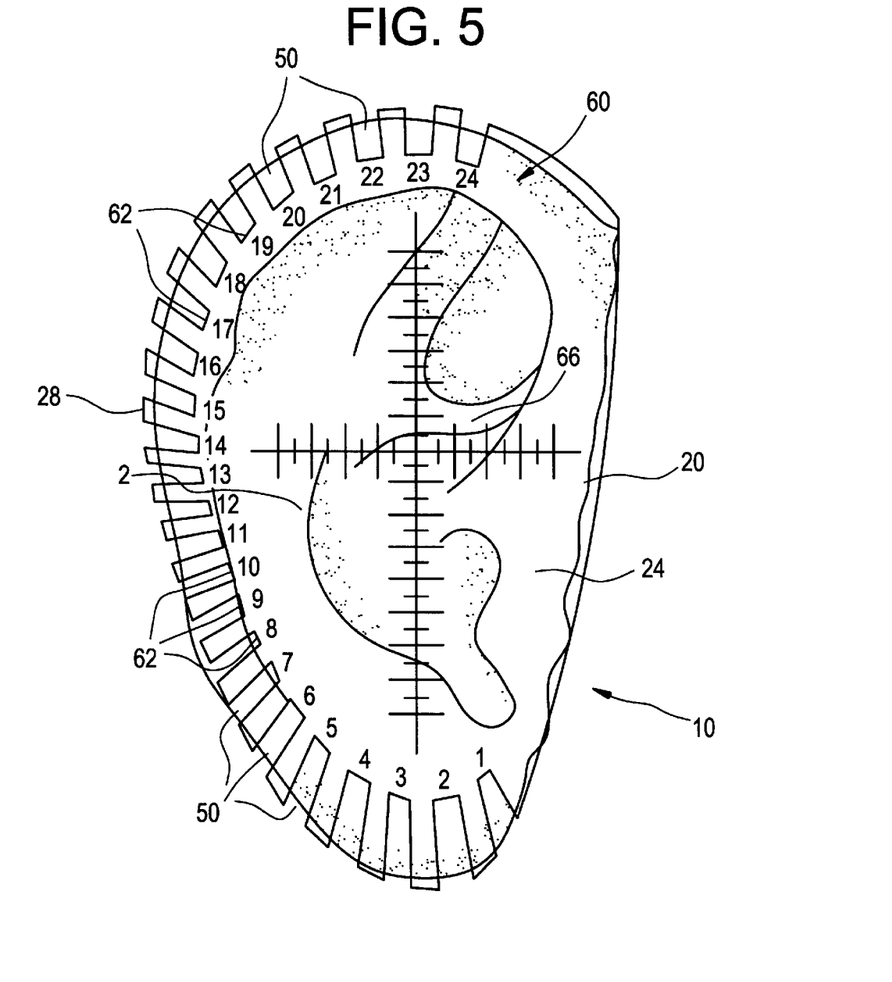
FIG. 5 is an elevational view showing the embodiment of FIG. 4 positioned against an ear.

FIG. 5 is a side elevational view of the embodiment shown in FIG. 4 with the ear piercing template apparatus 10 positioned on an ear 2. FIG. 5 helps show how the measurement markings 66 and the aperture labels 62 may be used to position the ear piercing template apparatus 10 on the ear 2 and the ear piercing device 80 in the proper aperture 50, or slot. Additionally, FIG. 5 reveals that the size and shape of the ear piercing template apparatus 10 is approximately the same as that of the ear 2 and how the slots are positioned about the ear 2 and their relative lengths. Further, as shown in the figure, one preferred embodiment of the ear piercing template apparatus 10 provides a body 20 formed of a transparent or semi-transparent material, such as certain plastics. Making the ear piercing template apparatus 10 of a transparent material aids proper positioning of the body 20 on the ear 2 and enhances accuracy and repeatability.

Figure 6:
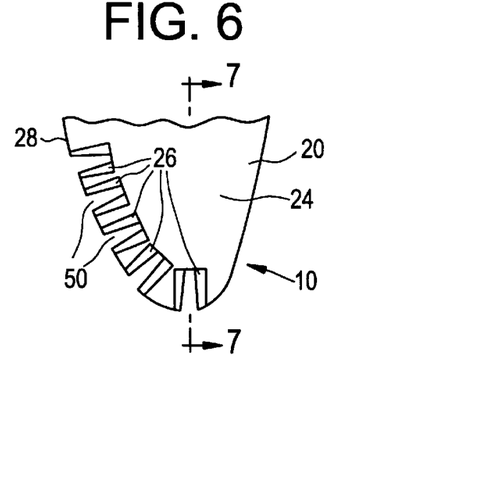
FIG. 6 is a partial front elevational view of an alternative embodiment of the ear piercing template apparatus.
Figure 7:
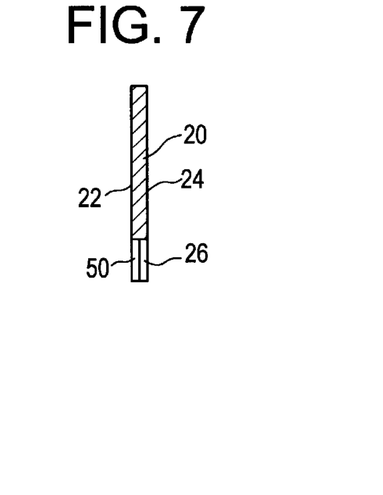
FIG. 7 is a sectional view taken along lines 7—7 in FIG. 6.

FIGS. 6 and 7 are front and side elevational views of one alternative embodiment respectively. As shown in the figures, apertures 50 comprise slots extending to the periphery 28 of the body 20. The body 20 defines a recess 26 about each of the apertures 50 that extends in from the outer surface 24 of the body 20 partially through the body 20. Thus, the recess 26 has an outer size that is larger than the aperture 50. Additionally, the size and shape of the recess 26 is similar to that of an outer clamp 84 of an ear piercing device 80 and is adapted to receive the outer clamp 84 therein. Therefore, in use, the forward face of the outer clamp 84 abuts the bottom of the recess 26 with the side walls of the recess 26 abutting the sides of the outer clamp 84. The aperture 50 is positioned within the recess 26 to provide for proper alignment with the stud 92 while the outer clamp 84 is in abutting engagement with the recess 26. When the outer clamp 84 is positioned within the recess 26, the ear piercing template apparatus 10 will not move relative to the ear piercing device 80. Accordingly, the recesses 26 about the apertures 50 help maintain the relative positions of the ear piercing template apparatus 10 and the ear piercing device 80.

Figure 8:
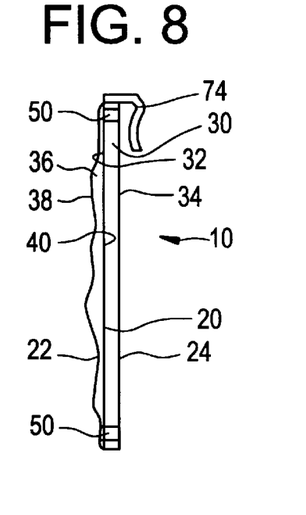
FIG. 8 is a side elevational view of an alternative embodiment of the ear piercing template apparatus.

FIG. 8 is another alternative embodiment of the present invention. In this embodiment, the body 20 of the ear piercing template apparatus 10 comprises a rigid member 30 and a cushion 36, each having an inner (32 and 38 respectively) and outer surface (34 and 40 respectively). The outer surface 34 of the rigid member 30 corresponds to that of the body 20; the inner surface 38 of the cushion 36 corresponds to that of the body 20; and the inner surface 32 of the rigid member 30 and the outer surface 40 of the cushion 36 are attached to one another. Preferably, the cushion 36 covers the full inner surface area of the rigid member 30. The rigid member 30 is substantially rigid and provides the desired rigidity for the ear piercing template apparatus 10 as previously discussed.

The cushion 36 is adapted for abutment with the ear. To facilitate the abutment and to provide additional comfort, the cushion 36 is preferably formed of a substantially resilient material that easily deforms when pushed against the ear. Examples of suitable materials include, inter alia, cotton and other cloths, foam or gel encased within a protective sac, a sponge or sponge-like material, or any other standard padding material. To provide additional comfort, one embodiment of the cushion 36 has the general shape and contour of the ear. Thus, the cushion 36 has a greater thickness in certain areas than others so that the cushion 36 abuts a greater surface area of the ear. In addition to providing improved comfort, the cushion 36, having a similar contour to the ear, may also provide increased accuracy due to the natural positioning of the contours of the cushion 36 to the contours of the ear. However, as the contours of various peoples' ears differ, the cushion 36 contours must be general and able to fit a great number of peoples' ears. Although individualized ear piercing template apparatuses 10 contoured to a particular individuals ears is possible, such a design is not preferred for general use.

However, one alternative embodiment and application of the ear piercing template apparatuses 10 includes adapting the cushion 36 to the particular individual to enhance the accuracy and repeatability of hole placement. If the cushion 36 is sufficiently thick and ductile in the center portion, the ear piercing template apparatus 10 can be pressed onto the ear and maintained on the ear by the cushion 36 (with the cushion 36 acting as the support member 70). If the recipient's ears are substantially similar to one another, moving the ear piercing template apparatus 10 with the cushion 36 formed to the shape of the first ear to the other ear will position the ear piercing template apparatus 10 in the same relative location. Other embodiments include making permanent (non-deformable) molds for an individual adapted to their particular ears.

Additionally, the embodiment of FIG. 8 provides a clip 74 attached to the top of the body 20 that is adapted to act as the support member 70. The clip 74 is a resilient member having an apogee end that is biased toward the body 20 of the ear piercing template apparatus 10. The clip 74 is adapted and positioned so that, when the ear piercing template apparatus 10 is positioned against the ear, the clip 74 extends behind the ear with the apogee end biased against the ear. Thus, the clip 74 holds the ear piercing template apparatus 10 to the ear and acts as the support member 70.

Figure 9:
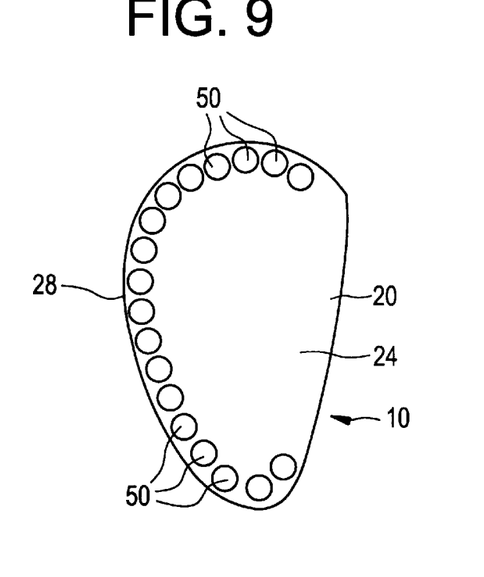
FIG. 9 is a front elevational view of another alternative embodiment of the ear piercing template apparatus.

FIG. 9 shows yet another alternative embodiment wherein the apertures 50 comprise holes through the body 20 of the ear piercing template apparatus 10. In this embodiment, the holes do not intersect the periphery 28 of the body 20. Therefore, the diameter of the hole must be greater than the outer diameter of the head 96 of the stud 92 to allow removal of the ear piercing template apparatus 10. However, to provide the desired support, the diameter of the hole is preferably smaller than the outer dimensions of the outer clamp 84 so that the inner face of the outer clamp 84 abuts the body 20 of the ear piercing template apparatus 10 during the ear piercing procedure.

Figure 10:
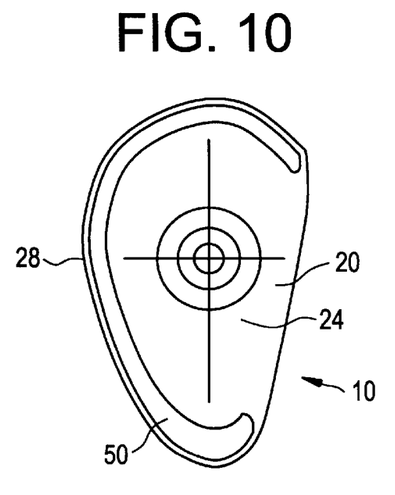
FIG. 10 is a front elevational view of yet another alternative embodiment of the ear piercing template apparatus.

FIG. 10 is a side elevational view of another embodiment of the ear piercing template apparatus 10. This embodiment has a single aperture 50 through the body 20 that comprises a slot extending parallel and proximal to the periphery 28 of the body 20. The slot preferably does not intersect the periphery 28 of the body 20 and extends about a portion of the body 20. The width of the slot is preferably sufficiently large that the ear piercing template apparatus 10 may be removed from about the stud 92 after the operation is complete. Thus, the width of the slot is preferably wider than the diameter of the stud 92. Alternatively, the portion of the body 20 between the periphery 28 and the slot is sufficiently flexible that the body 20 may be removed from about the stud 92 by first removing the body 20 to one side of the slot and, then, removing the body 20 to the other side of the slot.

FIG. 10 also discloses another type of indicia 60 on the surface of the body 20 that comprises a target-like indicia 60. The target provides a vertical and horizontal line intersecting one another at the approximate center of the surface. A plurality of circles having different diameters are centered about the point of intersection of the lines. Using the target, the operator may center the ear piercing template apparatus 10 about a certain point and use the circle to determine the approximate distance from some point. Preferably, the body 20 is at least semi-transparent.

Figure 11:
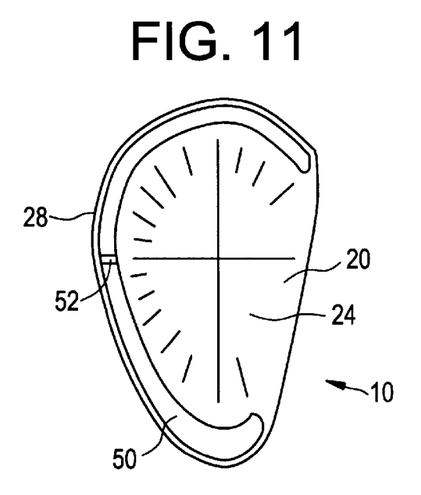
FIG. 11 is a front elevational view of still yet another alternative embodiment of the ear piercing template apparatus.

An embodiment similar to that of FIG. 10 shown in FIG. 11, includes a intermediate support 52 dividing the slot into two slots and affixing the portions of the body 20 on either side of the slot to one another. Also, the embodiment shown in the figure provides indicia 60 in the form of angle markings 64 that indicate the angle about an approximate center of the ear piercing template apparatus 10. The angle markings 64 help to position the pierced hole in the proper relative location on the ear.

Figure 12:
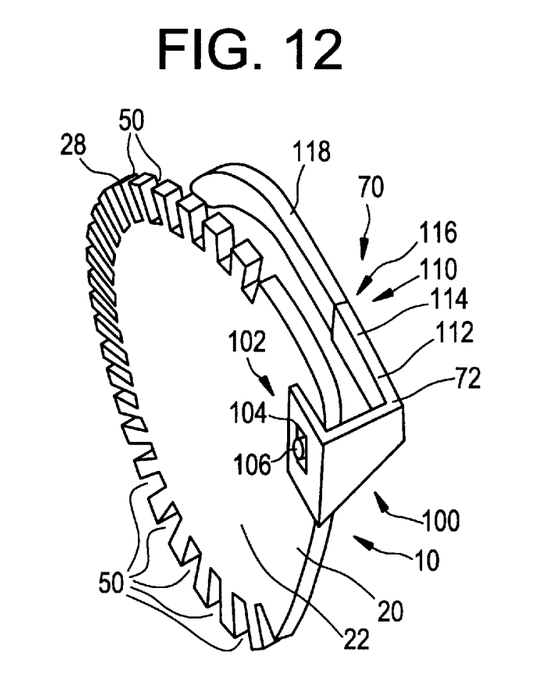
FIG. 12 is a perspective view of the ear piercing template apparatus embodiment having a position adjustment member.

FIG. 12 reveals yet another alternative embodiment for the ear piercing template apparatus 10 that incorporates an position adjustment member 100 that facilitates the adjustment of the position of the body 20 relative to the support member 70, the earpiece 72, and thus the ear. In the embodiment shown, the position adjustment member 100 is incorporated into the earpiece 72.

The earpiece 72 shown comprises a body member 112 having opposing ends. One end of the body member 112, the first end, is adapted for attachment to the body 20 of the ear piercing template apparatus 10 and incorporates a vertical adjustment member 102; the other, second end is adapted for attachment to an ear rest 118 and incorporates a horizontal adjustment member 110. The vertical and horizontal adjustment members 102, 110 comprise the position adjustment member 100 in the embodiment of FIG. 12. Proximal the first end of the body member 112, an adjustment slot 104 extends through the body member 112. The adjustment slot 104 is oriented vertically relative to the ground when the ear piercing template apparatus 10 is worn. An adjustment screw 106 extends through the adjustment slot 104 and into a mating hole (not shown) in the body 20 of the ear piercing template apparatus 10. The diameter of the head of the adjustment screw 106 is larger than the width of the adjustment slot 104 so that, when the adjustment screw 106 is tightened, it provides sufficient force to prevent the relative movement of the body 20 and the body member 112. However, when the screw 106 is loosened, the body 20 is free to move vertically (restricted only by the length of the adjustment slot 104) relative to the body member 112. Thus, the adjustment slot 104 and adjustment screw 106 provide for vertical adjustment of the body 20 relative to the earpiece 72 and, thus, the ear.

The second end of the body member 112 defines a cavity therein so that the second end defines a sleeve 114. The ear rest 118 extends slidably into the sleeve 114 of the second end. A position setter 116 within the sleeve 114 holds the ear rest 118 in the sleeve 114 and resists the movement of the ear rest 118 relative to the sleeve 114. However, the resistance to relative movement provided by the position setter 116 is relatively weak so that a user may easily adjust the relative position between the parts, but is sufficiently strong that the relative position will not change without the application of an outside force. The position setter 116 may take many embodiments, such as, inter alia, detents, a relatively tight fit between the parts, increased frictional surfaces, and the like. Thus, the ear rest 118 and the sleeve 114 defined buy the second end comprise the horizontal adjustment member 110 and allow the position of the ear piercing template apparatus 10 to be adjusted relative to the wearer's ear.

Although FIG. 12 shows one embodiment for the position adjustment member 100, many other possible variations and embodiments exist. However, such variations are considered a part of the scope of the present invention.

Figure 13:
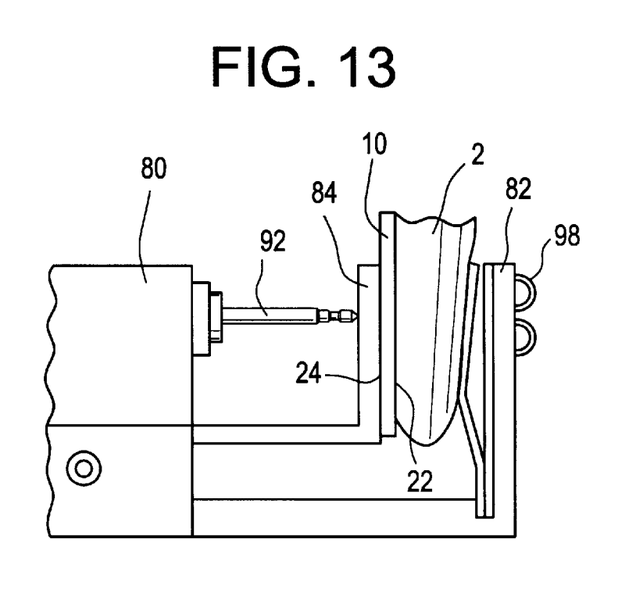
FIG. 13 is a side elevational view of the ear piercing template apparatus in use.

FIG. 13 is a partial side elevational of the ear piercing template apparatus 10 in use. When used, the operator positions the ear piercing template apparatus 10 against the ear 2 and attaches the support member 70 to maintain the position of the body 20. The position adjustment member 100 may be used to properly position the body 20 relative to the ear 2 or, in a system comprising a plurality of ear piercing template apparatuses 10, the correct one is selected and positioned. Once positioned, the operator, with the assistance of the customer, or recipient, determines the proper position for the pierce. Alternatively, the position may be selected prior to placing the ear piercing template apparatus 10 against the ear 2. Once the proper location of the pierce is identified, the ear piercing device 80 is positioned with the inner clamp 82 abutting the back of the ear 2 and the outer clamp 84 abutting the outer surface 24 of the ear piercing template apparatus 10 and with the stud 92 aimed at the pierce location. The ear piercing device 80 is then used to pierce the customer's ear 2. During the piercing, the proper angle of the hole through the ear 2 is easily attained due to the relatively rigid nature of the ear piercing template apparatus 10.

The ear piercing template apparatus 10 is then removed from the ear 2 and placed on and attached to the customer's other ear 2. The ear piercing template apparatus 10 may be aligned with the aid of the indicia 60 on the ear piercing template apparatus 10. Then, the position of the desired pierce location is determined by aligning the pierce with that on the opposite ear 2, already pierced. The indicia 60 as well as the apertures 50 of the ear piercing template apparatus 10 facilitate this alignment. After the correct position is found, the piercing process is repeated.

While the foregoing is directed to the preferred embodiment of the present invention, other and further embodiments of the invention may be devised without departing from the basic scope thereof, and the scope thereof is determined by the claims which follow.

I claim:

1. An ear piercing template apparatus for use with an ear piercing device of the type that uses a stud to pierce an ear, the apparatus comprising:

a body having opposing surfaces and a periphery;

at least one aperture extending through the body;

wherein the body and the at least one aperture are sized and adapted to provide passage of the stud therethrough;

the body having an outer surface and an inner surface;

the body defining a recess about each of the at least one apertures;

the recess formed in the outer surface; and the recess having a size and shape similar to that of an outer clamp of an ear piercing device and adapted to receive the outer clamp therein.

2. An ear piercing template apparatus for use with an ear piercing device of the type that uses a stud to pierce an ear, the apparatus comprising:

a body having opposing surfaces and a periphery;

at least one aperture extending through the body;

wherein the body and the at least one aperture are sized and adapted to provide passage of the stud therethrough; and wherein the body is at least partially transparent.

3. An ear piercing template apparatus for use with an ear piercing device of the type that uses a stud to pierce an ear, the apparatus comprising:

a body having opposing surfaces and a periphery;

at least one aperture extending through the body;

wherein the body and the at least one aperture are sized and adapted to provide passage of the stud therethrough; and wherein the body further comprises;

a rigid member having an inner surface and an outer surface;

a cushion having an inner surface and an outer surface the outer surface of the cushion attached to the inner surface of the rigid member;

the inner surface of the cushion defining an inner surface of the body and the outer surface of the rigid member defining an outer surface of the body;

the rigid member is substantially rigid; and the cushion is adapted for abutment with the ear.

4. The apparatus of claim 3, wherein the cushion is formed of a resilient material.

5. The apparatus of claim 3, wherein the inner surface of the cushion has a shape that substantially conforms to an ear.

6. An ear piercing template apparatus for use with an ear piercing device of the type that uses a stud to pierce an ear, the apparatus comprising:

a body having opposing surfaces and a periphery;

at least one aperture extending through the body;

wherein the body and the at least one aperture are sized and adapted to provide passage of the stud therethrough;

a support member attached to the body, the support member adapted to maintain the body on the ear; and, wherein the support member comprises an earpiece.

7. An ear piercing template apparatus for use with an ear piercing device of the type that uses a stud to pierce an ear, the apparatus comprising:

a body having opposing surfaces and a periphery;

at least one aperture extending through the body;

wherein the body and the at least one aperture are sized and adapted to provide passage of the stud therethrough;

a support member attached to the body, the support member adapted to maintain the body on the ear; and, wherein the support member comprises a clip.

8. An ear piercing template system for use with an ear piercing device of the type that uses a stud to pierce an ear, the system comprising:

a plurality of ear piercing apparatuses, the apparatuses each comprising:

a body having opposing surfaces and a periphery;

at least one aperture extending through the body; and wherein the body and the at least one aperture are sized and adapted to provide passage of the stud therethrough; and each of the plurality of ear piercing apparatuses having a different size from the others.

9. A method for piercing an ear using an ear piercing template apparatus and an ear piercing device of the type that uses a stud to pierce an ear, the method comprising:

positioning the ear piercing template apparatus against the ear with at least one aperture of a body of the ear piercing template apparatus aligned with the desired piercing location on the ear;

aligning a stud held within the ear piercing device with the desired piercing location on the ear; and actuating the ear piercing device to pierce the ear at the desired piercing location on the ear.

\* \* \* \* \*